United States Patent [19]

Bodor et al.

[11] 4,018,925

[45] Apr. 19, 1977

[54] METHOD OF ARRESTING BACTERIAL GROWTH WITH CERTAIN SELECTED DICHLORO-2,2,5,5-TETRASUBSTITUTED-3-6-PIPERAZINEDIONES

[75] Inventors: Nicolae S. Bodor; James J. Kaminski, both of Lawrence, Kans.

[73] Assignee: Interx Research Corporation, Lawrence, Kans.

[22] Filed: Apr. 10, 1975

[21] Appl. No.: 566,743

Related U.S. Application Data

[62] Division of Ser. No. 456,743, April 1, 1974, Pat. No. 3,891,649.

[52] U.S. Cl. .............................................. 424/250
[51] Int. Cl.² .......................................... A01N 9/22
[58] Field of Search .............. 260/268 DK; 424/250

[56] References Cited

UNITED STATES PATENTS 3,136,598  6/1964  Kokorudz .......................... 424/250
3,142,530  7/1964  Kokorudz .................. 260/268 DK

*Primary Examiner*—Albert T. Meyers
*Assistant Examiner*—D. W. Robinson
*Attorney, Agent, or Firm*—Charles N. Blitzer

[57] ABSTRACT

There is provided, novel N-chloramine compounds of the 1,4-dichloro-2,2,5,5-tetrasubstituted-3,6-piperazinedione type, having the formula:

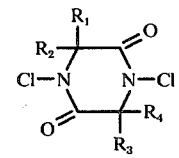

where $R_1$, $R_2$, $R_3$, $R_4$, which may be the same or different, each represent a member selected from the group consisting of an alkyl group of from 1 to 20 carbon atoms and an aryl group.

The compounds encompassed by the above generic formula exhibit antibacterial activity, but most importantly, the compounds encompassed within the above generic formula exhibit enhanced stability over the closest related prior art compounds, when such compounds are employed in aqueous solution for antibacterial application.

6 Claims, No Drawings

METHOD OF ARRESTING BACTERIAL GROWTH WITH CERTAIN SELECTED DICHLORO-2,2,5,5-TETRASUBSTITUTED-3-6-PIPERAZINEDIONES

CROSS-REFERENCE TO RELATED APPLICATIONS

This application is a divisional application of our earlier co-pending application, Ser. No. 456,743, filed 4/1/74, now U.S. Pat. No. 3,891,649.

BACKGROUND OF THE INVENTION

1. Field of the Invention

The present invention relates to certain novel N-chloramine compounds of the 1,4-dichloro-2,2,5,5-tetrasubstituted-3,6-piperazinedione type and more particularly, the present invention relates to such compounds, which exhibit excellent antibacterial activity. However, most importantly, these compounds exhibit enhanced stability over the closest related prior art compounds in aqueous solution.

2. Description of the Prior Art

U.S. Pat. No. 3,136,598 to Kokorudz (hereinafter "Kokorudz") discloses certain 1,4-dichloro-2,5-diketopiperazine compounds, in which the carbon atom, adjacent to the carbonyl group can contain two hydrogen atoms or in the alternative, a hydrogen atom in combination with a methyl or an ethyl group. These compounds are useful as antibacterial agents; in other words, such compounds can be employed in aqueous solution for the purpose of disinfection. In addition, the compounds described in this patent, due to their high chlorine potential, can also serve as effective bleaching agents, and more specifically, bleaching agents for textile fabrics, such as cottons. (See, U.S. Pat. No. 3,142,530.)

Applicants have extensively studied the compounds disclosed by kokorudz and have observed that while these compounds do exhibit excellent antibacterial activity in aqueous solution, such compounds when contained in an aqueous solution, are highly unstable. That is, when such compounds are introduced into an aqueous solution for application as antibacterial agents, such solutions must be used almost immediately as the compounds disclosed by Kokorudz will rapidly decompose, thus precluding sufficient germicidal activity to be achieved.

SUMMARY OF THE INVENTION

Accordingly, it is one object of the present invention to provide novel N-chloramine compounds of the 1,4-dichloro-2,2,5,5-tetrasubstituted-3,6-piperazinedione type, exhibiting sufficient antibacterial activity, i.e. germicidal and disinfecting activity.

Still, another object of the present invention is to provide novel N-chloramine compounds of the type described, where, in addition to such compounds exhibiting sufficient antibacterial activity, such compounds will exhibit a superior stability to those compounds described by Kokorudz.

Accordingly, the present invention is directed to the discovery of novel N-chloramine compounds of the 1,4-dichloro-2,2,5,5-tetrasubstituted-3,6-piperazinedione type, which have the formula:

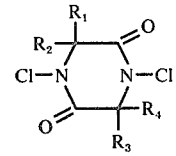

wherein $R_1$, $R_2$, $R_3$, $R_4$, which may be the same or different, each represent a member selected from the group consisting of an alkyl group of from 1 to 20 carbon atoms and an aryl group.

Illustrative alkyl groups are those of methyl, ethyl, propyl, butyl, pentyl, decyl, tetradecyl, hexadecyl, and eicosanyl and as illustrative aryl groups, phenyl, and naphthyl are exemplified. However, those alkyl groups containing 1–5 carbon atoms are preferred.

The unique stability exhibited by the compounds of the present invention as opposed to those compounds disclosed by Kokorudz results from the fact that the compounds of this invention do not contain any alpha-hydrogen atoms on the carbon atom adjacent to the carbonyl group of the compounds disclosed herein.

During applicants investigation of those compounds disclosed by Kokorudz, they observed a relationship between stability and the lack of alpha-hydrogen atoms on the carbon atom adjacent to the carbonyl group in the piperazinedione nucleus. In other words, applicants observed that when all alpha-hydrogens on the carbon atoms adjacent the carbonyl groups of the piperazinedione nucleus were substituted with alkyl groups of from 1 to 20 atoms and/or aryl groups, stability of such resulting compounds was enhanced when compared to the stability exhibited by Kokorudz's compounds.

DETAILED DESCRIPTION OF THE INVENTION

The compounds of the present invention can be prepared by a simple reaction scheme. Basically, these compounds are conveniently prepared by chlorinating the appropriate 2,2,5,5-tetrasubstituted-3,6-piperazinedione as illustrated below:

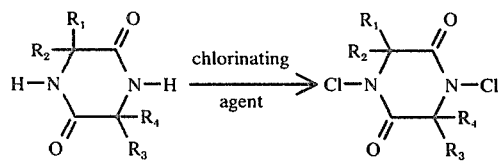

wherein $R_1$, $R_2$, $R_3$, and $R_4$ are defined above.

The chlorinating agent employed can be that of any conventional chlorinating agent and illustrative of such chlorinating agents are $Cl_2$, NaOCl, $Ca(OCl)_2$, t-BuOCl, and NCS.* However, it will be easily recognized by the skilled artisan that other chlorinating agents, which are conventional other than those described herein, can be employed with equal effectiveness for applicant's purpose.

* N-Chloro-succinimide

The 2,2,5,5-tetrasubstituted-3,6-piperazinedione precursors are readily prepared from the corresponding amino acid, amino acid ester, and/or the appropriate dipeptide following conventional procedures as described by J. P. Greenstein and M. Winitz in the text entitled "Chemistry of Amino Acids," Volume II, J. Wiley and Sons, Incorporated, New York, New York, 1961, Chapter 10.

The present invention will be better understood from a review of the following examples, which are simply illustrative and non-limitative of the present invention.

EXAMPLE 1 (PREPARATION OF 1,4-DICHLORO-2,2,5,5-TETRAMETHYL-3,6-PIPERAZINEDIONE)

Firstly, the precursor compound (2,2,5,5-tetramethyl-3,6-piperazinedione) was prepared from alpha-aminoisobutyric acid following the procedure described by S. M. McElvain and E. H. Pryde, "THE JOURNAL OF THE AMERICAN CHEMICAL SOCIETY", 71, 326(1949). Reference to the general procedure used is made in the Greenstein and Winitz article referred to earlier in this Application.

Once the 2,2,5,5-tetramethyl-3,6-piperazinedione precursor compound was isolated, the following procedure was initiated.

Through a mechanically stirred suspension of 29.95g (0.17 mol) of 2,2,5,5-tetramethyl-3,6-piperazinedione in 250 ml of water at 0° C, chlorine gas was bubbled therethrough for a period ranging from 1.5 to 2.0 hours. A white solid was isolated by filtration, washed thoroughly with cold water, and dried in vacuo over calcium sulfate to yield 38.20 g (0.16 mol) of 1,4-dichloro-2,2,5,5-tetramethyl-3,6-piperazinedione, 94% yield, m.p. 176.5°–178° C; I.R. (KBr)-1680cm$^{-1}$ (C=O).

Anal. Calculated for $C_8H_{12}Cl_2N_2O_2$ was as follows: C, 40.18; H, 5.06; N, 11.72; and Cl, 29.66. Found: C, 40.49; H, 5.18; N, 11.64 - and Cl, 28.71.

ANTIBACTERIAL ACTIVITY STUDIES

The procedure to determine the antibacterial activity of 1,4-dichloro-2,2,5,5-tetramethyl-3,6-piperazinedione was based primarily on a modification of the serial dilution method of analysis. However, instead of determining the minimum inhibitory concentration parameters for the compound investigated, applicants alternatively chose to determine the bactericidal endpoint for a given concentration of the compound investigated. Consequently, applicants studies were established to determine the time required for complete sterilization of the micro-organism tested, when exposed to a given concentration of the compound investigated.

The method and reagents employed in applicants antibacterial studies are described below:

| Organism | ATCC Code | Overnight Broth Culture(Organisms/ml) |
|---|---|---|
| Staph. epidermidis | 12228 | $5 \times 10^6$ |
| E. coli | 10536 | $10 \times 10^6$ |
| Kleb. pneumoniae | 10031 | $12 \times 10^6 - 13 \times 10^6$ |
| Pseud. aeruginosa | 9027 | $12 \times 10^6 - 13 \times 10^6$ |
| Staph. aureus | 6538 | $6 \times 10^6 - 8 \times 10^6$ |
| Bord. bronchiseptica | 4617 | $3 \times 10^6$ |

Nutrient Broth B.B.L. — 8g/1000 ml. distilled water. The broth contains 5g. gelysate peptone and 3g. beef extract. The solution has a pH of 6.9.

Nutrient Agar — 23g/1000 ml. distilled water. The nutrient contains 5g. gelysate peptone, 3g. beef extract and 15g. agar.

Horse Serum T.C. — 10% horse serum solution in distilled water. The serum solution was freshly prepared and adjusted to a pH of 7 using carbon dioxide prior to its use.

METHOD

A stock solution of the isolated compound (1,4-dichloro-2,2,5,5-tetramethyl-3,6-piperazinedione) was prepared using an appropriate buffered solution.

For screening in the absence of a denaturing agent (e.g., horse serum) an equal volume of distilled water and the resulting solution was subjected to the screen.

For screening in the presence of a denaturing agent, a volume of the stock solution was diluted using an equal volume of 10% horse serum. When necessary, the final solution was adjusted to the desired pH using 1N HCL and the solution was permitted to stand at room temperature for thirty minutes prior to the screening procedure.

To 5 ml. of the stock solution being evaluated, there was added 0.2 ml. of an overnight broth culture containing the particular micro-organism being investigated (see above). At time intervals of 0.5, 1, 2, 3, 4, 5, . . . minutes, a loop of this suspension was subcultured into 5 ml. of a sterile nutrient broth. All the samples were then incubated at 37° C for seven days with daily observation for evidence of bacterial growth. The time interval reported is for that sample in which no bacterial growth was observed after the incubation period.

Aside from the foregoing, several controls were also employed as described below.

CONTROL 1

This control was designed basically to insure viability of the overnight broth culture.

To 5 ml. of a sterile 0.9% sodium chloride solution, there was added 0.2 ml. of an overnight broth culture containing the particular micro-organism being investigated. A loop of this suspension was subcultured into 5 ml. of a sterile nutrient broth and incubated at 37° C for seven days.

CONTROL 2

This control was designed to insure that the dilution factor of the nutrient broth was beyond any bacteriostatic activity of the 1,4-dichloro-2,2,5,5-tetramethyl-3,6-piperazinedione.

To 5 ml of a sterile nutrient broth, there was added a loop of the 1,4-dichloro-2,2,5,5-tetramethyl-3,6-piperazinedione solution and the solution was mixed immediately. To this solution, there was then added a loop of an overnight broth culture which was diluted 25x with a 0.9% sodium chloride solution. Incubation was carried out for seven days at a temperature of 37° C.

CONTROL 3

This control was employed to insure the bacterial growth observed was that due to the organism being tested, rather than contamination from a foreign organism.

At the same time intervals used for subculturing the test solution into nutrient broth during the screening procedure, a loop of the test solution was also subcultured onto sterile nutrient agar plates. This technique was useful for observing the characteristic colonial morphology of each organism.

CONTROL 4

This control was used initially to insure that the pH of the solution and the concentration of the buffer species did not inhibit the bacterial growth during the time intervals used in the screening procedure.

The entire screening procedure was conducted for each buffered solution using the buffered solution rather than the 1,4-dichloro-2,2,5,5-tetramethyl-3,6-piperazinedione solution in the procedure.

The results of the antibacterial studies respective of 1,4-dichloro-2,2,5,5-tetramethyl-3,6-piperazinedione are set out on the following page in Table I.

TABLE I

| COMPOUND | CONDITIONS pH | DILUENT | CONCENTRATION DATA COMPOUND | POSITIVE Cl | ANTIBACTERIAL ACTIVITY TIME (MIN) 12228 | 10536 | 10031 | 9027 | 6538 | 4617 |
|---|---|---|---|---|---|---|---|---|---|---|
| 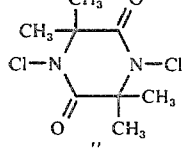 | 0.1M NaOAc pH4.6 | $H_2O$ | $0.59 \times 10^{-3}M$ | 41 PPM 139PPM | 2 | 1 | 2 | 3 | 3 | 1 |
| " | 0.1M NaOAc pH4.6 | Serum | $0.59 \times 10^{-3}M$ | 41 PPM 139PPM | >15 | >10 | >10 | >10 | >15 | >10 |
| " | 0.1M $NaH_2PO_4$ | $H_2O$ | $0.52 \times 10^{-3}M$ | 36 PPM | 2 | 1 | 4 | 5 | 4 | 3 |
| " | 0.1M $NaH_2PO_4$ pH7.0 | Serum | $0.52 \times 10^{-3}M$ | 36 PPM 126PPM | >15 | >15 | >15 | >15 | >15 | >15 |
| " | 0.1M $Na_2B_4O_7$ pH8.8 | $H_2O$ | $0.62 \times 10^{-3}M$ | 43 PPM 146PPM | 2 | 1 | 4 | 4 | 4 | 4 |

In addition, the following compounds as described in Table II below, will exhibit substantially, the same antibacterial activity observed for the compound 1,4-dichloro-2,2,5,5-tetramethyl-3,6-piperazinedione. These compounds can be prepared in accordance with those procedures previously outlined.

TABLE II

| $R_1$ | $R_2$ | $R_3$ | $R_4$ |
|---|---|---|---|
| $C_2H_5$ | $C_2H_5$ | $C_2H_5$ | $C_2H_5$ |
| $C_5H_{11}$ | $C_5H_{11}$ | $C_5H_{11}$ | $C_5H_{11}$ |
| $C_8H_{17}$ | $C_8H_{17}$ | $C_8H_{17}$ | $C_8H_{17}$ |
| $C_{10}H_{21}$ | $C_{10}H_{21}$ | $C_{10}H_{21}$ | $C_{10}H_{21}$ |
| $C_{12}H_{25}$ | $C_{12}H_{25}$ | $C_{12}H_{25}$ | $C_{12}H_{25}$ |
| $C_{15}H_{31}$ | $C_{15}H_{31}$ | $C_{15}H_{31}$ | $C_{15}H_{31}$ |
| $C_{20}OH_{41}$ | $C_{20}H_{41}$ | $C_{20}H_{41}$ | $C_{20}H_{41}$ |
| $CH_3$ | PHENYL | $CH_3$ | PHENYL |
| $C_2H_5$ | " | $C_2H_5$ | " |
| $C_5H_{11}$ | " | $C_5H_{11}$ | " |
| $C_8H_{17}$ | " | $C_8H_{17}$ | " |
| $C_{10}H_{21}$ | " | $C_{10}H_{21}$ | " |
| $C_{12}H_{25}$ | " | $C_{12}H_{25}$ | " |
| $C_{15}H_{31}$ | " | $C_{15}H_{31}$ | " |
| $C_{20}H_{41}$ | " | $C_{20}H_{41}$ | " |
| $CH_3$ | NAPHTHYL | $CH_3$ | NAPHTHYL |
| $C_2H_5$ | " | $C_2H_5$ | " |
| $C_5H_{11}$ | " | $C_5H_{11}$ | " |
| $C_8H_{17}$ | " | $C_8H_{17}$ | " |
| $C_{10}H_{21}$ | " | $C_{10}H_{21}$ | " |
| $C_{12}H_{25}$ | " | $C_{12}H_{25}$ | " |
| $C_{15}H_{31}$ | " | $C_{15}H_{31}$ | " |
| $C_{20}H_{41}$ | " | $C_{20}H_{41}$ | " |
| PHENYL | $CH_3$ | PHENYL | $CH_3$ |
| " | $C_2H_5$ | " | $C_2H_5$ |
| " | $C_5H_{11}$ | " | $C_5H_{11}$ |
| " | $C_8H_{17}$ | " | $C_8H_{17}$ |
| " | $C_{10}H_{21}$ | " | $C_{10}H_{21}$ |
| PHENYL | $C_{12}H_{25}$ | PHENYL | $C_{12}H_{25}$ |
| " | $C_{15}H_{31}$ | " | $C_{15}H_{31}$ |
| " | $C_{20}H_{41}$ | " | $C_{20}H_{41}$ |
| NAPHTHYL | $CH_3$ | NAPHTHYL | $CH_3$ |
| " | $C_2H_5$ | " | $C_2H_5$ |
| " | $C_5H_{11}$ | " | $C_5H_{11}$ |
| " | $C_8H_{17}$ | " | $C_8H_{17}$ |
| " | $C_{10}H_{21}$ | " | $C_{10}H_{21}$ |
| " | $C_{12}H_{25}$ | " | $C_{12}H_{25}$ |
| " | $C_{15}H_{31}$ | " | $C_{15}H_{31}$ |
| " | $C_{20}H_{41}$ | " | $C_{20}H_{41}$ |
| $CH_3$ | $C_2H_5$ | $C_5H_{11}$ | $C_8H_{17}$ |
| $C_8H_{17}$ | $C_5H_{11}$ | $C_2H_5$ | $CH_3$ |
| $C_2H_5$ | $CH_3$ | $C_8H_{17}$ | $C_5H_{11}$ |
| $C_5H_{11}$ | $C_8H_{17}$ | $CH_3$ | $C_2H_5$ |
| $C_2H_5$ | $C_8H_{17}$ | $C_{12}H_{25}$ | $C_{15}H_{31}$ |
| $C_{15}H_{31}$ | $C_{12}H_{25}$ | $C_8H_{17}$ | $C_2H_5$ |

TABLE II-continued

| $R_1$ | $R_2$ | $R_3$ | $R_4$ |
|---|---|---|---|
| $C_8H_{17}$ | $C_2H_5$ | $C_{15}H_{31}$ | $C_{12}H_{25}$ |
| $C_{12}H_{25}$ | $C_{15}H_{31}$ | $C_2H_5$ | $C_8H_{17}$ |
| $C_8H_{17}$ | $C_{12}H_{25}$ | $C_{15}H_{31}$ | $C_{20}H_{41}$ |
| $C_{20}H_{41}$ | $C_{15}H_{31}$ | $C_{12}H_{25}$ | $C_8H_{17}$ |
| $C_{15}H_{31}$ | $C_{20}H_{41}$ | $C_8H_{17}$ | $C_{12}H_{25}$ |
| $C_{12}H_{25}$ | $C_8H_{17}$ | $C_{20}H_{41}$ | $C_{15}H_{31}$ |
| $C_5H_{11}$ | $C_{12}H_{25}$ | $C_{15}H_{31}$ | $C_{20}H_{41}$ |
| $C_{20}H_{41}$ | $C_{15}H_{31}$ | $C_{12}H_{25}$ | $C_5H_{11}$ |
| $C_{12}H_{25}$ | $C_5H_{11}$ | $C_{20}H_{41}$ | $C_{15}H_{31}$ |
| $C_{15}H_{31}$ | $C_{20}H_{41}$ | $C_5H_{11}$ | $C_{12}H_{25}$ |
| PHENYL | PHENYL | PHENYL | PHENYL |
| NAPTHYL | NAPTHYL | NAPTHYL | NAPTHYL |
| NAPTHYL | PHENYL | NAPTHYL | PHENYL |
| PHENYL | NAPTHYL | PHENYL | NAPTHYL |
| PHENYL | $C_{12}H_{25}$ | PHENYL | $C_{12}H_{25}$ |
| " | $C_{15}H_{31}$ | " | $C_{15}H_{31}$ |
| " | $C_{20}H_{41}$ | " | $C_{20}H_{41}$ |
| NAPHTHYL | $CH_3$ | NAPTHYL | $CH_3$ |
| " | $C_2H_5$ | " | $C_2H_5$ |
| " | $C_5H_{11}$ | " | $C_5H_{11}$ |
| " | $C_8H_{17}$ | " | $C_8H_{17}$ |
| " | $C_{10}H_{21}$ | " | $C_{10}H_{21}$ |
| " | $C_{12}H_{25}$ | " | $C_{12}H_{25}$ |
| " | $C_{15}H_{31}$ | " | $C_{15}H_{31}$ |
| " | $C_{20}H_{41}$ | " | $C_{20}H_{41}$ |
| $CH_3$ | $C_2H_5$ | $C_5H_{11}$ | $C_8H_{17}$ |
| $C_8H_{17}$ | $C_5H_{11}$ | $C_2H_5$ | $CH_3$ |
| $C_2H_5$ | $CH_3$ | $C_8H_{17}$ | $C_5H_{11}$ |
| $C_5H_{11}$ | $C_8H_{17}$ | $CH_3$ | $C_2H_5$ |
| $C_2H_5$ | $C_8H_{17}$ | $C_{12}H_{25}$ | $C_{15}H_{31}$ |
| $C_{15}H_{31}$ | $C_{12}H_{25}$ | $C_8H_{17}$ | $C_2H_5$ |
| $C_8H_{17}$ | $C_2H_5$ | $C_{15}H_{31}$ | $C_{12}H_{25}$ |
| $C_{12}H_{25}$ | $C_{15}H_{31}$ | $C_2H_5$ | $C_8H_{17}$ |
| $C_8H_{17}$ | $C_{12}H_{25}$ | $C_{15}H_{31}$ | $C_{20}H_{41}$ |
| $C_{20}H_{41}$ | $C_{15}H_{31}$ | $C_{12}H_{25}$ | $C_8H_{17}$ |
| $C_{15}H_{31}$ | $C_{20}H_{41}$ | $C_8H_{17}$ | $C_{12}H_{25}$ |
| $C_{12}H_{25}$ | $C_8H_{17}$ | $C_{20}H_{41}$ | $C_{15}H_{31}$ |
| $C_5H_{11}$ | $C_{12}H_{25}$ | $C_{15}H_{31}$ | $C_{20}H_{41}$ |
| $C_{20}H_{41}$ | $C_{15}H_{31}$ | $C_{12}H_{25}$ | $C_5H_{11}$ |
| $C_{12}H_{25}$ | $C_5H_{11}$ | $C_{20}H_{41}$ $c_{15}H_{31}$ | |
| $C_{15}H_{31}$ | $C_{20}H_{41}$ | $C_5H_{11}$ | $C_{12}H_{25}$ |
| PHENYL | PHENYL | PHENYL | PHENYL |
| NAPHTHYL | NAPHTHYL | NAPHTHYL | NAPHTHYL |
| NAPHTHYL | PHENYL | NAPTHYL | PHENYL |
| PHENYL | NAPTHYL | PHENYL | NAPTHYL |

STABILITY STUDIES

The stability of the compound, 1,4-dichloro-2,2,5,5-tetramethyl-3,6-piperazinedione in aqueous solution was determined by (1) following the disappearance of the positive chlorine concentration of the N-Chloramine solution iodometrically and/or (2) following the decrease in the absorbance at the maximum wavelength spectrophotometrically.

The data obtained was interpreted in terms of a first order kinetic process and the half-life of said compound was reported in units of time at the condition under which they were determined.

The half-life studies between the compound 1,4-dichloro-2,2,5,5-tetramethyl-3,6-piperazinedione and the prior art compound, 1,4-dichloro-2,5-piperazinedione (per Kokorudz) are found in Table III reproduced below.

TABLE III
STABILITY ANALYSIS OF N-CHLORAMINES

| COMPOUND | SOLVENT | CONDITIONS : TEMPERATURE | HALF-LIFE(MIN) |
|---|---|---|---|
| 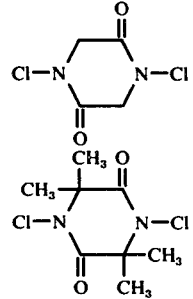 | 0.1M NaOAc pH 4.6 | 40 | 930 |
| | 0.1M NaH$_2$PO$_4$ pH 7.0 | 40 | 53 |
| | 0.1M Na$_2$B$_4$O$_7$ pH 9.3 | 40 | 43 |
| 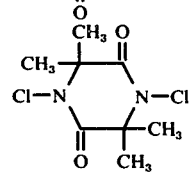 | 0.1M NaOAc pH 4.6 | 40 | 184,320 |
| | 0.1M NaH$_2$PO$_4$ pH 7.0 | 40 | 19,890 |
| | 0.1M Na$_2$B$_4$O$_7$ pH 9.3 | 40 | 2280 |

As is readily apparent, at the same pH (4.6, 7.0 and 9.3), a compound of this invention, 1,4-dichloro-2,2,5,5-tetramethyl-3,6-piperazinedione) exhibited far greater stability (half-life) than the compound of the prior art (1,4-dichloro,2,5-piperazinedione.)

As a result thereof, the compounds of this invention are far more suitable for commercial application, as aqueous solutions of such compounds can remain stable over much longer periods of time, whereas an aqueous solution of the prior art compound would have to be employed for antibacterial purpose rapidly, in order that antibacterial activity can be exhibited before degradation or decompositon of the compound occurs. With the compounds of the present invention, stable aqueous solutions are provided, thus permitting the user to employ such solutions for achieving an antibacterial effect over a much longer period of time than that under which aqueous solutions of the prior art compounds could be employed.

As with the antibacterial activity studies, the compounds set out in Table II, will also exhibit similar stability values as exhibited by 1,4-dichloro-2,5-piperazinedione (using the same procedure outlined above)

As indicated earlier, the uniqueness of the present invention resides in the fact that the compounds disclosed herein exhibit enhanced stability in aqueous solution over the closest related prior art compounds and in addition, the compounds of this invention exhibit effective antibacterial activity as well. The key to the enhanced stability exhibited by the compounds of the present invention resides in the fact that no alpha-hydrogen atoms are maintained on the carbon atom adjacent the carbonyl group of the piperazinedione nucleus.

As any skilled artisan will understand, the solubility of the compounds of the present invention, in aqueous solution will vary, depending upon the chain length of the alkyl group and further depending upon whether an aryl moiety is introduced. However, any skilled artisan can recognize that for those compounds encompassed within applicants' generic formula, which exhibits limited water solubility, such problems can easily be overcome by introducing a suitable conventional solubilizing agent into the aqueous system. As an example, any surfactant, compatible with the N-Chloro functionality, will suffice for applicants' purpose.

These compounds are conveniently used in aqueous solution. They may be applied by any conventional means, e.g., spray, wipe, etc.

Although the present invention has been adequately described in the foregoing specifications and Examples included therein, it is readily apparent that various changes and/or modifications can be made thereto without the departing from the spirit and scope thereof.

What we claim is:

1. A method of arresting bacterial growth which comprises applying to the same, an effective antibacterial amount of a compound of the formula:

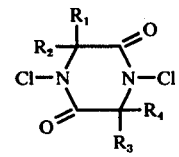

wherein R$_1$, R$_2$, R$_3$, and R$_4$ are the same or different, and represent a member selected from the group consisting of an alkyl group of from 1 to 20 carbon atoms, a phenyl group, and a naphthyl group.

2. The method of claim 1, wherein said compound is 1,4-dichloro-2,2,5,5-tetramethyl-3,6-piperazinedione.

3. The method of claim 1, wherein said compound is 1,4-dichloro-2,2,5,5-tetraethyl-3,6-piperazinedione.

4. The method of claim 1, wherein said compound is 1,4-dichloro-2,2,5,5-tetrapropyl-3,6-piperazinedione.

5. The method of claim 1, wherein said compound is 1,4-dichloro-2,2,5,5-tetrabutyl-3,6-piperazinedione.

6. The method of claim 1, wherein said compound is 1,4-dichloro-2,2,5,5-tetrapentyl-3,6-piperazinedione.

* * * * *